United States Patent [19]
Tan

[11] Patent Number: 5,290,273
[45] Date of Patent: * Mar. 1, 1994

[54] LASER TREATMENT METHOD FOR REMOVING PIGEMENT CONTAINING LESIONS FROM THE SKIN OF A LIVING HUMAN

[76] Inventor: Oon T. Tan, 1 Marlborough St., Boston, Mass. 02116

[*] Notice: The portion of the term of this patent subsequent to Jun. 8, 2010 has been disclaimed.

[21] Appl. No.: 66,875

[22] Filed: May 25, 1993

Related U.S. Application Data

[63] Continuation-in-part of Ser. No. 743,797, Aug. 12, 1991, Pat. No. 5,217,455.

[51] Int. Cl.$^5$ .............................................. A61B 17/36
[52] U.S. Cl. ........................................... 606/9; 606/2; 606/3; 606/13; 128/898
[58] Field of Search .................... 128/878; 606/3, 2, 9, 606/13

[56] References Cited

U.S. PATENT DOCUMENTS

| | | | |
|---|---|---|---|
| 4,316,467 | 2/1982 | Muckerheide | 606/9 |
| 4,718,416 | 1/1988 | Nanumi | 606/9 |
| 4,854,320 | 8/1989 | Dew | 606/9 X |
| 5,000,752 | 3/1991 | Hosrin et al. | 606/9 |
| 5,057,104 | 10/1991 | Chess | 606/9 |
| 5,059,192 | 10/1991 | Zaias | 606/9 |
| 5,217,455 | 5/1993 | Tan | 606/9 |

*Primary Examiner*—Peter A. Aschenbrenner
*Attorney, Agent, or Firm*—David Prashker

[57] ABSTRACT

A laser treatment method is provided which removes pigment containing lesions, both normal and abnormal medically, from the skin of a living human. The methodology comprises a carefully controlled irradiation of the chosen treatment site on the skin of a living human; avoids the creation of cosmetically disfiguring scars; and eliminates the typical hypopigmentation as well as the pitting and other changes in skin texture normally accompanying conventionally known laser treatment techniques.

7 Claims, 1 Drawing Sheet

LASER TREATMENT METHOD FOR REMOVING PIGEMENT CONTAINING LESIONS FROM THE SKIN OF A LIVING HUMAN

CROSS-REFERENCE

This application is a Continuation-In-Part of U.S. patent application Ser. No. 743,797 filed Aug. 12, 1991, now U.S. Pat. No. 5,217,455.

FIELD OF THE INVENTION

The present invention is directed to a method for removing pigmentations, lesions, and abnormalities from the skin of a living human using light from a laser and its delivery system; and is particularly directed to the use of the Alexandrite laser apparatus under carefully controlled conditions for the removal of epidermal and dermal tissues as occurs both in nature and by intervention.

BACKGROUND OF THE INVENTION

Among the more common conditions shared by humans generally is the presence of lesions on the skin, many of which contain pigments in one or more colors and some of which are considered abnormal although not always dangerous to the individual. Typical examples of naturally occurring pigmentations include freckles; age or liver spots; birthmarks; malignant melanomas; nevi (melanocytic, epidermal, vascular, and connective tissue); and lentigines (brown spots on the skin or mucous membrane). In addition, a person's skin may have discoloring abnormalities due to vascular lesions which are caused by an abundance of enlarged blood vessels. Common examples of discolorful vascular lesions are "port wine" stain birth marks; telangiectasis, a colored spot formed most commonly on the skin by a dilated capillary or other small blood vessel; and hemangioma, a highly visible benign tumor composed of well-formed blood vessels and classified as capillary or cavernous.

In comparison, intervention created pigment containing lesions are commonly called "tattoos" and are commonly divided into two different categories: human-caused tattoos and traumatic-inflicted tattoos. Traumatic-inflicted tattoos are created typically as a result of accidents or other mishaps which cause scrapes, abrasions, explosion, or lacerations in a manner such that foreign material inadvertently becomes embedded into the skin. During the healing process, the skin becomes pigmented and often scarred as a result. In comparison, human-created tattoos are a popular form of skin decoration and self-expression in many cultures and societies. A common example here in the U.S. is the tattooed sailor; and it has been estimated that as many as 10% of the U.S. general population have tattoos somewhere on the skin of their bodies.

It will be recognized and appreciated that many persons at some point in their lives wish to remove pigment containing lesions, whether normal or abnormal, from their skin for health and/or cosmetic reasons. Even those individuals who voluntarily choose to create pigmented patterns on their skin may subsequently in their lives choose to undergo treatment designed to remove the pigmented lesion—often because of advancing age, or via a change in lifestyle, or as a consequence of a new personal relationship. Presently existing modes of removal treatment may achieve some clearing or lightening of pigment containing skin areas but only at substantial risk to the individual because of severe changes to the natural pigmentation and coloring of the skin or by incurring actual scarring of the treated skin area. The risks and severity of the multiple problems and consequences associated with removing pigmentations and other lesions generally of the skin is represented and illustrated by the difficulties of removing tattoos. However, it is explicitly understood that tattoos are merely one prototypic example of the different pigment containing lesions known which require removal.

As is the circumstance with many kinds of pigment containing lesions, the pigment lies inside the skin (i.e., the dermis or epidermis) and destructive modes of treatment have been employed conventionally to remove this pigment. Thus, a major problem of known treatments has been access to the epidermal or dermal pigment; and the only way it has been possible to remove the pigment(s) without using laser apparatus has been to remove all the skin around the pigmented lesion from the most exterior surface downwards into the deep tissues.

The conventional modes of treatment used for removal of pigmented lesions generally thus presently include: surgical excision and skin graft; dermabrasion; saliabrasion; cryosurgery; and laser light generated by $CO_2$, argon, Nd:YAG, and ruby lasers [Hirshowitz, D. E., *Plast. Reconstr. Surg.* 373–378 (1980); Scutt, R. W. B., *Br. J. Hosp. Med. J.* 8:195 (1972); Manchester, G. H., *Curtis* 7:295 (1971); Clabaugh, F. M., *Plast. Reconstr. Surg.* 55:401 (1975); McDowell, F., *Plast. Reconstr. Surg.* 53:580 (1974); and Groot et al., *J. Am. Acad. Dermatol.* 15:518–522 (1986)]. While each of these modes of treatment has its own committed group of adherents, practitioners, and supporters, all of them unfortunately create as many problems as they cure concomitant with using the conventionally known procedures.

For example, a well recognized problem and drawback with some presently known laser treatment methods is that these routinely cause damage to both pigmented and non-pigment cells in the skin without discriminating between them. Laser treatment of pigment containing skin lesions has varied markedly from merely the superficial to extreme depth in the skin with little attempt to control the kind or the amount of tissue and cells destroyed. Moreover, some laser treatment processes known to date almost always cause a major change in skin texture; the skin is thus substantially altered from being smooth, elastic, and mobile to being hard and immobile and to becoming bumpy, cratered, or even pitted. In addition, conventional laser treatments cause a loss of the normal skin markings (normal ridges and valleys) as well as changes in normal skin pigmentation (losses as well as increases in normal skin color). Therefore, the resulting change in skin texture is almost always accompanied by a consequential change in skin color in which the skin at the treated site is no longer normal in pigmentation. Instead, the treated skin site appears either porcelain-white or mottled with dark pigment, both of these conditions resulting from either loss of all pigment or the implanting of pigment in the dermis instead of the epidermis. All of these radical and undesirable consequences and changes result from extensive, severe damage induced by the presently known laser treatment modalities and treatment methods.

Even the ruby laser (the best of the conventionally used laser systems) and the known procedures using the ruby laser have been demonstrated to be flawed, deficient, and inefficient for removing pigmentations, lesions, and abnormalities from the skin of a living human. As has well been described in the art, there are many problems and deficiencies concomitant with or caused by the ruby laser system and its various modes of use. In one mode, the ruby laser emits its laser light pulses called a normal pulse Another known way to operate and use the ruby laser is in the Q-switched mode; short bursts of pulses are emitted called a pulse train. A pulse train becomes problematic when the pulses are of low power. When this occurs, provided the pulses are discharged frequently enough and in spite of the short pulses being in the nanosecond range, the effect on the living tissue is similar to that of a continuous wave (CW) laser, which produces a highly indiscriminate effect. Moreover, instead of destroying the targeted structure with each pulse and, because the ruby energy output is low, there is only sufficient energy to partially alter the pigment containing lesion. Also, due to the characteristics of the ruby laser itself, the intensity of each pulse burst can meaningfully vary and it is very difficult for the practitioner to control the light energy dose delivered to each laser exposed site.

In addition, there presently is no convenient or easy way of precisely delivering the laser light beam to the patient. A common way of performing this manipulation at present is by the use of an articulating arm which is not only cumbersome but also easily goes out of alignment. This difficulty results in a further decrease of laser energy available to destroy the targeted tissue, thus making the ruby laser system even less efficient for removing abnormal pigmentations. Also, when used in the non-Q switched mode the ruby laser often produces severe scarring of the skin.

Another way to operate and use the ruby laser system conventionally is in the Q-switched mode. In this alternative mode of use, a single energy pulse of short duration (nanoseconds) is delivered to the skin by the ruby laser. However, despite the usage of Q-switched ruby lasers in clinical studies since the 1960's, the only currently available means of delivering treatment energy pulses in this manner is again by means of an articulated arm which is not only difficult to align and is bulky, but also creates "hot spots" within the delivered light beam area. One reported study revealed that multiple treatments using the ruby laser in the Q-switched mode removed at least 90% of the normal coloration in the skin. Adverse effects of hyper- and hypo-pigmentation were noted in some patients; and pigmented lesion sites composed of colors other than blue-black were not affected directly but instead showed a severe whitening of the skin as a result of this treatment [Read et al., *Br. J. Plast. Surg.* 36:455-459 (1983)]. Another study [Taylor et al., *Arch. Dermatol.* 126:893-899 (1990)] reported substantial lightening or total clearing of skin in 78% of amateur tattoos and 23% of 13 professional tattoos. However, this report demonstrated that multiple re-treatments were required; transient hypopigmentation was seen in 50% of treated skin sites; and notable scarring appeared in approximately 6% of treated patients.

It is not surprising, therefore, that there is major interest in developing new and improved laser delivery systems which may be used in a carefully controlled method and treatment procedure for removing pigmentations from the skin of a living human. It will be recognized and appreciated also that while the development of new laser equipment and new laser delivery systems constitutes one discrete area of technical research, such efforts are meaningfully different and distinct from other investigations directed to developing a clinical process and methodology under carefully controlled operational parameters which would be effective and usable by a dermatologist or other medical practitioner. Equally important, the development of a clinically effective therapeutic treatment using a carefully controlled laser apparatus and laser delivery system which would prevent hypo-and/or hyperpigmentation as well as avoiding cratering/pitting and elevation or destruction of dermal and/or epidermal layers of the skin would be generally recognized as a major improvement and advance by practicing dermatologist and clinicians treating patients on a regular basis.

SUMMARY OF THE INVENTION

The present invention constitutes a laser treatment method for removing pigment containing lesions from the skin of a living human, said method comprising the steps of:

irradiating on a first occasion a chosen treatment site on the skin of a living subject of about 1-100 millimeters in diameter with a beam of pulsed light from a laser delivery system, said pulsed light having a wavelength from about 700-1,100 nanometers, fluences of about 1-50 Joules per square centimeter, and a pulse duration of about 1-300 nanoseconds;

maintaining said irradiation to disrupt at least one pigment containing lesion on the chosen treatment site on the skin of the living human until a color change endpoint on the skin surface is achieved by said laser light treatment while largely avoiding the destruction of normal skin structures and cells;

allowing the skin at said irradiated treatment site to heal for a time period not less than about 7 days and not more than about 70 days; and then irradiating on at least one subsequent occasion the chosen treatment site on the skin of the living human with another pulsed beam of laser light having a wavelength from about 700-1,100 nanometers, fluences of about 1-50 Joules per square centimeter, and a pulse duration of about 1-300 nanoseconds, said subsequent irradiation occasion being repeated as necessary to achieve substantial clearance of the chosen treatment site on the skin.

BRIEF DESCRIPTION OF THE FIGURE

The present invention may be more easily and completely understood when taken in conjunction with the accompanying drawing, in which.

DETAILED DESCRIPTION OF THE INVENTION

Figure 1:
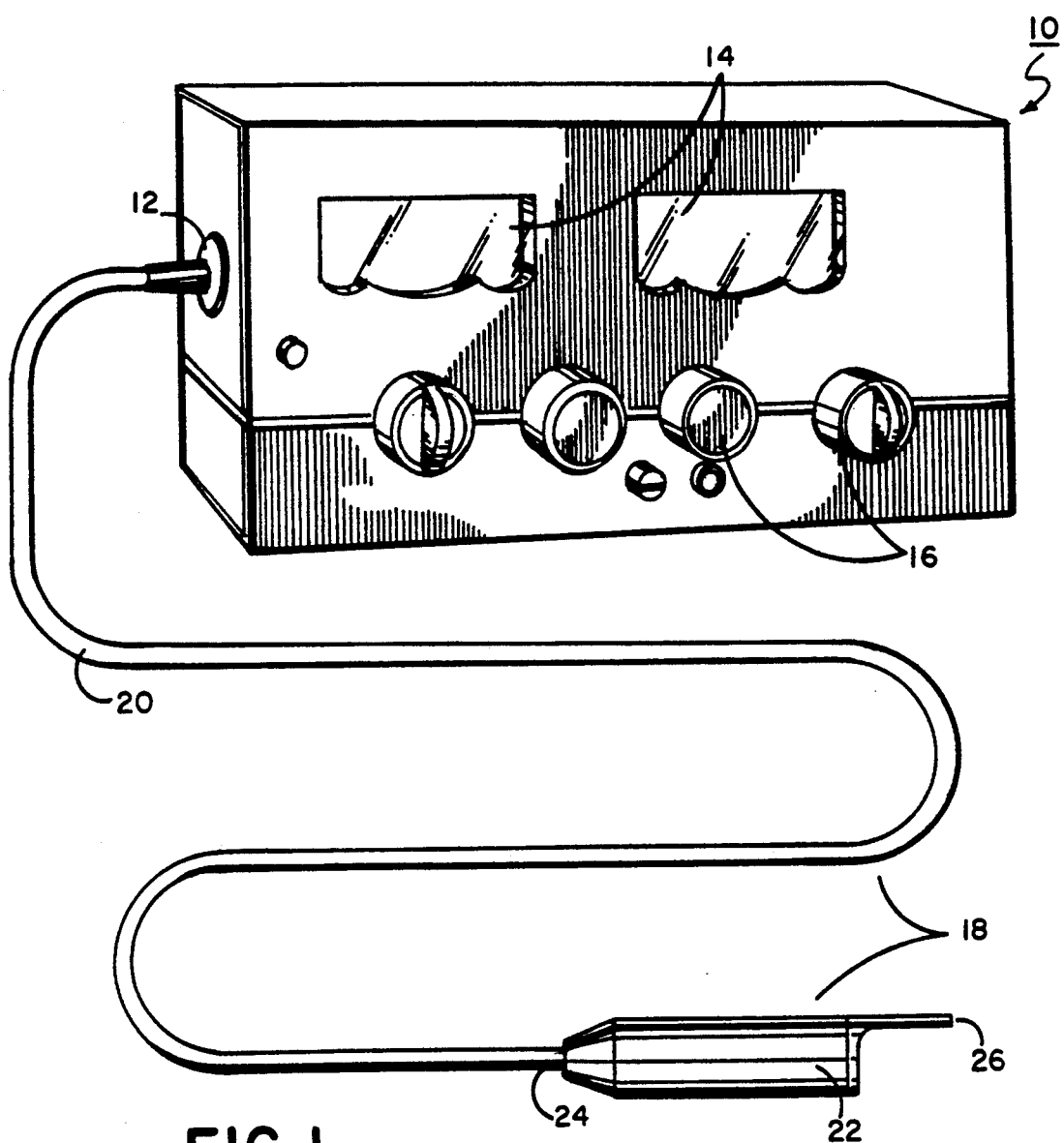
FIG. 1 is an illustrative view of an unmodified Alexandrite laser apparatus.

The present invention is a clinical treatment methodology to be used by clinical dermatologists and other medical practitioners for the removal of pigmentations, lesions, and abnormalities from the skin on a living human. This treatment method employs a laser apparatus and a laser delivery system having specified engineering capabilities able to provide carefully controlled light wavelengths which can be directed at chosen treatment sites on the skin of a living human. Since the methodology intrinsically requires the existence and availability of a laser apparatus having specified capabilities and engineering specifications, descriptive details will be provided herein identifying at least one such laser apparatus which can be modified to provide the specific operating parameters needed in order to perform the treatment methodology efficiently and successfully. Nevertheless, the treatment methodology comprising the manipulative steps of the present invention are not dependent on one particular type or class of laser equipment; and is not restricted to any particular engineering specifications or apparatus designs as such. To the contrary, the present treatment methodology is intended to be and is capable of employing lasers of any type or capacity so long as the specific parameters demanded by the treatment are provided in a predictable and controlled manner. Hence, it will be clearly understood that the present methodology is not dependent on any particular laser equipment or system; and cannot be said to be an outgrowth or derivative of any particular laser apparatus or laser system regardless of how such technology was developed.

The present therapeutic treatment methodology is a dermatological technique suitable for use generally in a variety of different clinical applications. A representative, but non-exhaustive listing of applications and uses for the treatment methodology are identified by Table 1 below.

TABLE 1

DERMATOLOGICAL APPLICATIONS AND USES

(i) Removal of tattoos (professional and non-professional):
(ii) Epidermal and dermal pigment(s) removal: The pigment in these lesions can be either endogenous or exogenous. The latter can be substances injected into the body which are subsequently absorbed by specific structures in the skin and enhances the absorption of the delivered laser light.
(iii) Removal of melanin pigment from mucosae:
(iv) Ablation of skin: removal of skin tissue.
(v) Removal of superficial, benign, cutaneous, melanin pigmented lesions:
(vi) Removal of foreign matter in the skin including endogenous substances (such as calcium deposits) and exogenous matter (such as lead, gravel, shrapnel, etc.):
(vii) Removal of skin tumors, both benign and malignant (such as epidermal nevus):

A number of major advantages and conveniences are provided by the present treatment method. These include the following:

1. The present methodology is intended to be performed as a series of repeated treatments spaced in time from each other at preselected intervals as chosen by the physician with regard to the individual responses of his patients. Each occasion for treatment (from first to last) will provide an irradiation of the chosen treatment site on the skin of the living human under carefully controlled conditions and include treatment safeguards for exposure based upon the size, condition, and health of the individual's skin. Thus, the therapeutic process is tailored to the individual's particular response to each treatment and medical status; is employed over defined skin areas in limited degree without causing major destruction of the surrounding normal tissues and cells; and provides for periods of skin healing within the planned cycles and timing for the method from beginning to end.

2. The treatment method intends that the targeted treatment site on the skin of the living human be exposed to carefully chosen wavelengths of light energy, energy density, and exposure time. If the introductory occasions of irradiation reveal themselves to be insufficient cumulatively to achieve partial or substantial removal of the pigmentation, lesions, or abnormality from the chosen skin site; then the timing, energy density, and duration of light exposure can be increased or decreased incrementally as needed on an individual basis until the intervention has been able to achieve the desired goal of selective pigment removal. In this manner, the personal health, safety, and cosmetic appearance of the skin are affected only to the least extent required; and the side-effects of treatment such as scarring or general disfigurement of skin tissues are minimized.

3. The present treatment process provides a means for delivering the laser energy specifically to targeted zone alone. Because of the particular laser parameters used, the laser light bypasses normal non-targeted skin structures and cells. The methodology provides a means by which the destruction of normal skin structures and cells is largely avoided, eliminating loss of skin structures such as hair, sweat glands, pigment-containing cells and the hardening of tissues at the treatment site.

4. The present methodology also provides for a definitive color change at the skin surface immediately following laser irradiation which serves as an indicator that the correct treatment dose has been delivered to that skin area. This is of paramount importance to the clinician. Firstly, the clinician knows exactly the true location where the laser beam has been delivered to the skin. Having such a definitive clinical endpoint on the treated skin surface prevents the clinician from exposing the area to multiple irradiations (i.e., summation of doses or even missing areas of the lesion altogether). Secondly, the clinician is effectively informed by the immediate color change whether the correct and sufficient dose of laser energy has been delivered to the treatment site.

5. The present treatment method provides means of avoiding and eliminating "whitening" or hypopigmentation as well as hyperpigmentation of the skin—both of which have been the frequent and typical consequence of previously known and conventionally employed laser treatment procedures. The present invention provides clear and definite criteria by which the blanching and destruction of normal skin tissues and normal pigment containing cells is largely avoided, with the added consequence that the typical whitening and abnormal skin appearance is generally eliminated as a concomitant result.

6. The present treatment method also avoids and eliminates large-scale destruction of the chosen treatment site and the surrounding normal cells and tissues. Immediately following laser irradiation. The focal craters usually formed in the stratum corneum and/or epidermis at each irradiated site, the exudation of tissue fluid from these sites, and the crusting as well as the blistering, are all avoided by this treatment method. Therefore, the potential of developing infection of the treated site, which can also potentially enhance scar formation, is further avoided. Moreover, because the tissue injury being induced by this method is specifically restricted and confined to the pigment containing lesion, there is no change in skin texture from being smooth to "bumpy" or even pitted. Similarly, there are no cosmetically disfiguring scars when the methodology is performed in its preferred format.

7. Another major advantage of the present treatment method is that the epidermis in the irradiated area of skin remains intact. This not only decreases the potential risk of infection but also simplifies the management of post-operative wound care. Moreover, because the skin surface is intact and the treated skin area does not exude serum from the site to form crusts, this reduces the need to protect the treated skin with dressings for several weeks. Instead, the treated skin area need only be protected for between 2-7 days. Finally, because the skin surface remains intact, the possibility of the patient infecting the health care professional through skin structures containing infected viral particles or through infected exudate such as blood or serum are minimized.

In order to provide an accurate, comprehensive, and easily understood description generally and in detail of the present treatment methodology, it is both useful and convenient to focus periodically on a single application or emphasize a particular usage in order to illustrate specific points for the method. It will be expressly recognized and understood, however, that all such focused or emphasized description is also expressly representative and illustrative of the other intended applications, usages and treatments generally, and especially those listed within Table 1 previously herein; and that a focused disclosure in detail is merely one instance and setting of the broad scope of treatment applications encompassed by this method for use by dermatologists and clinicians generally. With this understanding in mind and to achieve this goal, the detailed disclosure will be presented in the following format and sequence: a description of the laser apparatus, hardware modifications, and operation parameters which are necessary for the successful treatment and removal of pigment containing lesions; a description of treatment details important for general clinical use and application; a step-by-step protocol for treatment use by the dermatologist or clinician; and a presentation of multiple case histories of treatment with human subjects for the removal of various kinds of pigment containing lesions in accordance with the present invention.

I. Laser Apparatus, Hardware Modifications, and Critical Laser Parameters

Since a useful description of laser apparatus will require a familiarity and understanding of laser equipment generally, its capabilities, and the terminology conventionally understood by laser engineers, a set of defined terms and use conditions are provided hereinafter in order to facilitate comprehension and depth of understanding.

Definitions

Pigment containing lesion (PCL): The presence of cells or organelles containing pigment in concentrates which are either significantly greater or when clustered together appear darker than normal. This makes the skin containing this collection of "pigment" appear darker compared to surrounding normal adjacent skin. Moreover, these pigment containing cells/organelles could be located in areas which, under normal circumstances, do not contain these cells/organelles such as the dermis.

Clearance: A value of the laser's ability to disrupt and remove a sufficient amount of dye, ink, or other pigments and to return a pigmented area of skin to near normal appearance as determined by visual inspection and/or photography.

Lightening: An evaluation of the laser's ability to disrupt and remove a sufficient amount of dye, ink, or other pigments and to return a pigmented area of skin to near normal appearance as determined by visual inspection and/or photography.

Wavelength: The frequency of the light energy with respect to the spectrum. Wavelengths of radiation in or near the visible region are expressed variously in Angstroms, micrometers, and nanometers. For the present treatment methodology, the wavelengths of light delivered by the laser are limited to the range from 700-1,100 nanometers.

Pulse Duration: The time interval (typically measures in nanoseconds) over which the laser light beam strikes the chosen treatment site on the skin of the living human. For purposes of the present treatment method, the pulse duration is limited to the range of about 1-300 nanoseconds.

Fluence: The energy density provided by the light beam as applied to the chosen or targeted treatment site on the skin of the living human. The energy density is measured with respect to the surface area and is stated in units of Joules per square centimeter or "$J/cm^2$". The present treatment method intends that a range of fluence from about 1-50 Joules per square centimeter be available for use with the concomitant capability to gradually and incrementally increase the energy density from 1 to 50 Joules per square centimeter at will or as needed.

Spot Size: The size or area of the chosen or targeted treatment site on the skin of the individual human which is measured in millimeters of diameter. The intended spot size can range from about 1-100 millimeters in diameter with a preferred range of from 1-8 millimeter diameter in most instances initially.

Peak and Average Power: The total amount of energy available from the laser head as determined by the engineering specifications and capabilities of the laser design. For purposes of the present treatment methodology, a peak power of from 5-50 megawatts from the laser head is desirable. A repetition rate of up to 5 Hz is desirable, allowing for an average power of up to 5 watts.

Delivery System: The physical means for delivering the beam of laser light from the laser apparatus to the chosen or targeted treatment site on the skin of the living human patient. This term includes all necessary or desirable equipment, controls, and engineering needed to provide the laser operating parameters critical for successful treatment.

The Preferred Laser Apparatus

The preferred laser apparatus is an Alexandrite laser in the Q-switched mode which provides laser pulses in a time duration in the rage of 1-300 nanoseconds; light wavelengths in the red range of the electromagnetic spectrum of about 700-1,100 nanometers; a system for delivering the laser light beam from the laser apparatus to the chosen or targeted treatment site on the skin of the living patient; and, preferably, a handpiece attached to the delivery system for controlling the delivery of the light beam from the laser system to the chosen treatment site on the skin of the patient with a spot size which is variable and ranges from 1-100 millimeters in diameter. The human case histories presented subsequently herein and the individual treatments described there were performed using the Alexandrite laser system provided by Candela Laser Corporation (Wayland, Mass.). The minimal Alexandrite laser apparatus was then modified as described herein to meet the critical conditions and operating parameters required by the present treatment methodology. Although any number of different laser apparatus and systems potentially can be modified in principle and in design to provide the necessary parameters and conditions required for use within the present treatment method, it is the individual modifications of the Alexandrite laser and delivery system which are described in detail herein as the representative apparatus preferably used to perform the therapeutic treatment.

Figure 2:
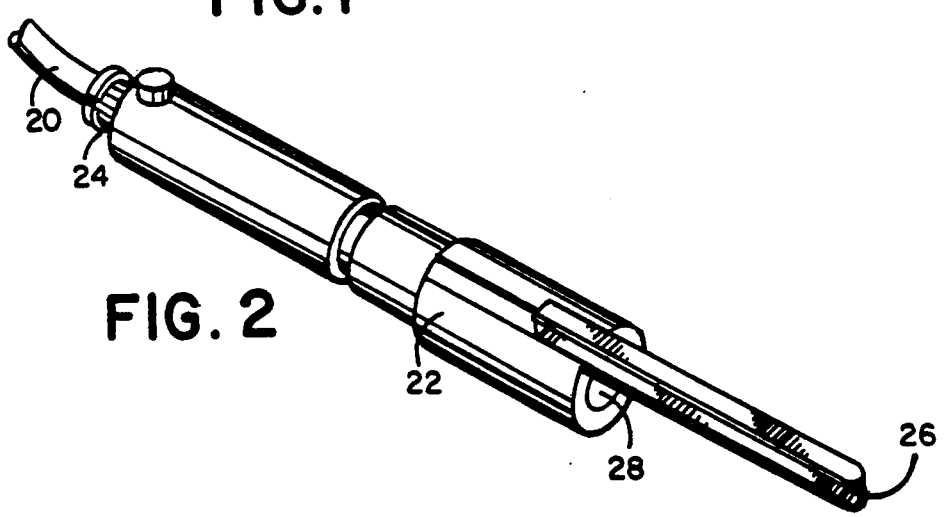
FIG. 2 is a detailed view of the delivery system for the Alexandrite laser apparatus of FIG. 1.

The typical Alexandrite laser delivery system is shown in FIGS. 1 and 2. The apparatus 10 comprises a laser head 12, a high voltage power supply 14, a distilled water circulator (not shown), a control system 16, and a delivery system 18. The laser head contains the cavity mirrors, Pockel's cell, solid-state laser medium (the Alexandrite rod), and two high intensity xenon flashlamps which excite the laser medium. Also incorporated in the laser head is a low power continuous wave red helium-neon laser. The outputs of the Alexandrite and helium-neon lasers are directed into optical components which combine and focus the laser radiation into the delivery system 18.

The delivery system 18 consist of a flexible light guide 20 with a handpiece 22 at its distal end 24. The handpiece 22 incorporates a distance gauge 26 which is placed against the skin of the person to ensure proper focusing of the laser beam on the chosen area of treatment. The output of the red helium-neon laser serves to locate the focal point 28 of the handpiece on the skin; and a footswitch (not shown) is then used to deliver a focused pulse of Alexandrite laser radiation to the chosen treatment site targeted by the helium-neon laser.

The high voltage power supply charges a set of storage capacitors which provide energy to the flashlamps. Depressing the footswitch initiates a trigger pulse which causes the capacitors to discharge through the flashlamps. The resulting flash excites the Alexandrite rod, causing the emission of a pulse of laser energy. The energy of the pulse is determined by the energy stored by the capacitors. A low power DC discharge is maintained in the lamps between pulses by a simmer circuit.

The temperature of the Alexandrite rod must be controlled for efficient lasing to be achieved. Circulation of heated, distilled water around the rod regulates the temperature and also serves to cool the flashlamps. The circulator unit which pumps the heated water through the flashlamp/rod assembly ahs a reservoir that is maintained at the desired temperature. A display on the circulator allows the temperature of the water to be monitored.

The physician controls the fluence (energy density) using a 10-turn knob on the control panel of the high voltage power supply to select the voltage on the capacitors. This control panel is also used to enable or disable the triggering of the laser (by turning on or off the high voltage inverter), and to start the flashlamp simmer current prior to triggering the laser.

The Alexandrite laser apparatus is desirably equipped with interlocks that turn off the high voltage power supply to prevent lasing when the cover of the laser head is opened or when the distilled water level in the circulator reservoir is low. Representative apparatus specifications are provided by Table 2 below.

TABLE 2

| APPARATUS SPECIFICATIONS | |
|---|---|
| Laser Type: | Flashlamp excited Alexandrite laser |
| Wavelength: | 700–1,100 nm ± 10 nm |
| Method of Optical Output: | Lens coupled light guide, articulating arm or optical fiber |
| Mode of Output: | Multimode |
| Operating Mode: | Single pulse operation |
| Maximum Delivered Output Energy: | 1–50 Joules/pulse |
| Spot Size: | 1–100 mm |
| Pulse Characteristic: | |
| Rate: | Single pulse (1.0 Hz maximum) |
| Duration: | 1–300 nanoseconds |
| Energy Source: | Flashlamps |

II. Hardware Modifications and Laser Operating Parameters

Certain laser operating parameters are critical for the successful treatment of pigment containing lesions. These include:

a. a pulse duration (exposure time) in the one to hundreds of nanoseconds range (1–300 nanoseconds);

b. a light wavelength in the red range of the electromagnetic spectrum (700–1,100 nm);

c. average power of 1–20 watts from the laser head;

d. a delivery system for delivering the laser light from the laser to the patient which might take the form of a light-guide, articulating arm, or an optical fiber; and e. a handpiece for delivery of the laser light from the delivery system which can be placed at fixed distances from the skin surface of the patient to ensure that spot size ranging from 1–100 mm in diameter are being delivered.

III. General Treatment Procedures and Preferred Details

A wide variety of different pigmentations, normal and abnormal, can be successfully treated using the Q-switched Alexandrite laser. The pigment colors which respond best are black and blue. However, green, red, and purple have also been effectively removed.

The Alexandrite laser apparatus should be Q-switched to provide pulse durations of from 1–300 nanoseconds, and preferably between 50–200 nanoseconds. The spot size of the laser beam ranges between 1–100 millimeters in diameter and desirably is from 3–5 millimeters in diameter. The light wavelength should desirably be around 760 nanometers. The energy densities used for irradiation treatment should begin in the range from 2.0 to 10.0 Joules per square centimeter, but may be 1–50 Joules per square centimeter on any occasion or as the individual's needs demand.

Specific pigmentation colors of the particular lesion (i.e., black, blue, etc.) should be identified, localized, and nominated as test sites. Specific energy densities (Joules per square centimer) used as test energy densities should be chosen and used to treat these small areas of the pigment containing lesion as initial test sites. The skin should either be grayish-white and even slightly reddened immediately following laser exposure of that test area. If the skin retains its normal skin tone after the laser exposure, then the energy density or fluence should be increased by 0.5–1.0 Joules per square centimeter until the skin surface becomes grayish-white and reddened and swollen. This change in skin color should occur immediately (up to ten minutes) after laser exposure.

The skin surface (epidermis) should remain intact. If the laser dose is too high, blisters or punctured holes in the stratum corneum or skin surface will appear. This will be accompanied by redness and swelling of the surrounding area at each of the laser irradiated sites will be evident. The laser exposed site should be protected from being traumatized by the application of a small non-adherent dressing. The patient should be asked to return for the next treatment visit at any time between one to ten weeks afterwards for evaluation of the irradiated test site.

At the second or subsequent visit, the test skin area previously irradiated is assessed for:

(a) meaningful color changes (i.e., lightening, clearance, or no change) of the laser treated site. A notation should also be made of the color of the immediately adjacent normal skin color;

(b) a skin texture change (i.e., elasticity, rigidity of the skin);

(c) a change in surface skin markings (i.e., the normal surface ridges and valleys of the skin disappear when scarring occurs); and (d) the presence or absence of adnexae (skin appendages) such as hairs before and after irradiation.

The laser exposed skin color as well as the color change(s) in the pigment containing lesion itself should be carefully examined and compared to adjacent normal and non-treated skin color. If the skin color in the laser treated area appears abnormal (procelain white, gray, or mottled brown) compared to untreated normal skin color, this suggests that the dose used for the first treatment is too high. By contrast, if the treated area remains totally unchanged, then insufficient laser energy has been delivered to the pigment containing lesion. In addition, the treated lesion skin site should feel as elastic and mobile as the normal untreated adjacent skin.

The goal of the treatment methodology is to lighten and eventually clear the pigment containing lesion with successive and repeated laser treatments, and at the same time, leave the surrounding normal skin intact and unaffected. However, if no change in the color of the pigment containing lesion at the test site has been noted at the first return visit, then an additional test area and test irradiation should be performed at a higher laser dose (by increasing the energy density of the light beam by 0.5-1.0 Joules per square centimeter). The same process of test site pigmentation assessment should be performed again as outlined above subsequently at between one to ten weeks following laser irradiation. Evaluation of test sites should continue to be performed using increasing energy densities until substantial lightening and/or clearance of the test site pigmentation lesion is achieved.

Note carefully, however, if one or more significant changes in the skin comprising any of the features outlined above are observed, then the energy density should be decreased and additional test site assessments should be performed until the "ideal" treatment dose (i.e., the minimum laser fluence required to produce lightening and/or clearance) is achieved.

Once the correct fluence has been determined (i.e., the best energy density and timed exposure producing lightening of the skin pigmentation with minimal alteration to normal skin)—that fluence should be used to treat a large area of the pigment containing lesion of the same color in that individual. Following this practice, separate skin areas, section by section, of the pigment containing lesion are then repeatedly irradiated individually on multiple occasions until the entirety of the lesion has been removed.

IV. Step-by-Step Preferred Protocol for Treatment

The following protocol is provided as the best procedure presently available for the removal of pigment containing lesions. It will be clearly recognized and understood, however, that this preferred protocol is but a model format for many others which would vary in some details but which retain the essential and critical features of the methodology generally.

History and Examination

A careful history should be taken to establish when and how the pigment containing lesion occurred on the skin of the patient. In addition, it should be established whether other treatment modalities have been used at any time previously in an attempt to remove the pigment containing lesion. Details of the prior treatment and the modalities used should be documented.

Examination should consist of a description of the actual size of the lesion, the "colors" or type of pigmentation presented, the presence or absence of any abnormal skin textures or typography including scars or other abnormal pigmentation which are present. Photographs should desirably be taken of the pigment containing lesion prior to irradiation treatment and at each subsequent visit and irradiation treatment session.

Treatment Protocol

Two to three small areas (approximately 1-3 square centimeters of each pigmented color, if appropriate) should be delineated. These will be designated as the test site areas. Several test doses (e.g., 2.5, 3.0, 4.0, 5 or 6 Joules per square centimeter) should be used to irradiate each of the different test sites. The skin should turn white/gray immediately or within ten minutes following laser light exposure. If the pigment containing lesion remains unchanged in color when fluences greater than 6 $J/cm^2$ are delivered, the laser output should be checked using an energy meter. If the output is correct, then a slightly higher fluence will be required. One should increase the fluence only by about 0.5 Joules per square centimeter as necessary and look out for the development of whitening/graying on the irradiated skin. If necessary, fluences of 10-50 $J/cm^2$ may be employed. The typical fluence to be used for the test site should initially be less than 5 or 6 $J/cm^2$ at a spot size of 3-5 millimeters in diameter. Care should be taken that the epidermis at the treatment site remains intact after the irradiation exposure dose.

Following skin irradiation, a topical antibiotic ointment is preferably applied to the treated site and the skin area protected using a non-adherent dressing. Such topical antibiotic ointments include Bacitracin, Neosporin, Polysporin, and Sulphadene. Alternatively, a topical cream such as Vitamin E cream may be used in place of the antibiotic ointment. Daily applications of the topical antibiotic ointment and dressings to the treated site should be advocated for approximately one week or until such time as the discoloration on the skin disappears.

The patient should be scheduled to return anytime between one and ten weeks afterwards for subsequent evaluation of pigmented color change, i.e., lightening of the pigment containing lesion with minimal change in normal skin color and any alternations in skin texture. A preferred time interval for the return visit is between 3-7 weeks. If the laser irradiated test site appears lightened at the return visit, the lowest dose (fluence) producing the best lightening of the skin should be used to irradiate the same pigmented area again as well as other areas of the lesion having the same color using the same laser fluence and pulse duration as before. However, if one or more of the test sites have been unresponsive to the initial laser test dose, a higher fluence (increased preferably 0.5–1.0 Joules per square centimeter) should be used at other test sites.

The same regimen of repeated irradiations over multiple visits should be instituted and completed until a satisfactory dose producing lightening of the skin lesion sites is established. If no change is observed at the different test sites following one or more exposure using fluences of 5 to 10 Joules per square centimeters, then it is likely that the particular color in the lesion will be unresponsive to this laser.

Once a satisfactory laser fluence and irradiation exposure has been determined, different sections of the pigment containing lesions(s) are then separately irradiated. Those treated skin areas which have lightened in meaningful degree following laser exposure should be irradiated again at one to ten week intervals repeatedly. It is likely that it will be necessary to increase the laser fluence periodically to remove the remnants of the pigmentation as it decreases in size and color. Irradiation of the entire pigment containing lesion section by section, should be repeated until the lesion pigments are completely cleared. In order to achieve this, it may be necessary t increase the laser fluence to as much as 20–50 Joules per square centimeter on subsequent visits repeatedly.

V. Human Case Reports

To demonstrate and empirically illustrate both the range and variety of pigment containing lesions efficaciously treated using the present methodology, a series of case history reports using human patients are provided. Moreover, merely as a demonstrative aid and as a representative showing of the many different applications intended for the present invention, three different kinds of pigment containing lesions are presented and summarized.

A. Treatment of benign cutaneous pigmented lesions

Case History No. 1

A 20 year old white caucasian female with a large cafe au lait (CAL) extending from her right thigh to her mid calf was tested at 3.0 and 4.0 $J/cm^2$ using the q-switched Alexandrite laser (760 nm) at a spotsize diameter of 3 mm and a pulse duration of 100 nsec. There was slight decrease in pigment at the treated sites when they were examined 6–8 weeks after the initial laser exposure. The same area was retreated at 6.0 $J/cm^2$ using the q-switched Alexandrite. Eight to nine weeks later, the Alexandrite laser treated areas were lighter than the adjacent areas of untreated CAL. New areas of untreated CAL were treated using the Alexandrite laser at 3.0 and 4.0 $J/cm^2$. These produced lightening of the birthmark when the patient returned for follow-up approximately 6 weeks later. Further treatments were delivered to lighten/clear the CAL using fluences of between 2.5 and 4.5 $J/cm^2$ at 760 nm. All of the treated areas lightened following laser irradiation.

Case History No. 2

The patient was a 32 year old female with a cafe au lait (CAL) on her left back. Three test sites were exposed to 3.5 $J/cm^2$ at 760 nm, 100 nsec, 3 mm diameter spotsize. Some lightening was observed at one of the three test sites. Two of the three areas were retreated using the Alexandrite laser at between 3.5 and 6.0 $J/cm^2$ on multiple occasions at 4–12 weekly intervals which produced substantial lightening of the CAL.

Case History No. 3

An eight year caucasian female presented herself for treatment with a large cafe au lait (CAL) on her right thigh. A test area was retreated after six weeks at the same fluence which produced further lightening. Because of the size of the lesion, the CAL was divided into small sections and each area was treated and retreated at fluences between 4.0 and 6.0 $J/cm^2$. Retreatments to the areas were performed at between 6 and 12 weekly intervals. Each treatment was followed by lightening of the treated site.

Case History No. 4

A 30 year old caucasian female with a cafe au lait (CAL) on her right buttock had two different test areas delineated. Both test areas of the CAL were exposed to the q-switched Alexandrite laser, one at a fluence of 4.0 and the other at 5.0 $J/cm^2$. For each test area, the pulse duration was 100 nsec at spotsize diameter of 3 mm. No change in either test area was observed following exposure to these fluences. A further third test area was then exposed to the ruby laser (694 nm) at 3.0 $J/cm^2$ (maximum fluence available), a 3 mm diameter and a pulse duration of approximately 20 nsec. No lightening was noted at the ruby laser irradiated site.

Because no change was noted at 5.0 $J/cm^2$ following exposure of the CAL to the Alexandrite laser, the whole lesion was exposed to 5.5 $J/cm^2$. The treated areas either lightened or cleared—"breaking up" the uniformly macular lesion into islands of hyperpigmentation with normal skin in between these islands when the patient was examined 6 weeks after this laser treatment. The remnants of the CAL were treated on four further occasions, at 6 weekly intervals between treatments, at fluences of 6.0 $J/cm^2$ using the q-switched Alexandrite laser (760 nm) at a pulse duration of 100 nsec and a spotsize of 3 mm diameter. The totality of these treatments cleared the CAL, leaving normal appearing skin at the Alexandrite laser irradiated sites.

Case History No. 5

A 24 year old caucasian female was treated who had two hyperpigmented lesions on her left calf which had been present since birth. Clinically, these lesions were consistent with the diagnosis of cafe au lait (CAL). Two test areas were delineated within the lesion—one test area was exposed to 4.0 $J/cm^2$ and the other to 3.0 $J/cm^2$—each using the Alexandrite laser at pulse durations of between 50 and 100 nsec and a spotsize of 3 mm diameter. When she was examined six weeks after the initial laser exposure, both test areas had lightened. Both the remaining CAL areas were treated and retreat at a fluence of 5.0 $J/cm^2$ at 6 weekly intervals for three further treatments. Then, five further retreatments were delivered to the same lesions at a fluence of 6.5 $J/cm^2$, again spaced at 6 weekly intervals. One of the five further treatments was delivered at 7.0 $J/cm^2$. Both the lesions were completely cleared when she returned for a follow-up visit.

Case History No. 6

A 40 year old caucasian female with a 4 year history of melasma was tested at 4.0 and 6.0 $J/cm^2$ using the q-switched Alexandrite laser at a pulse duration of 100 nsec and a spotsize of 3 mm diameter. The area treated at 6.0 $J/cm^2$ and retreated at intervals of between 6–9 weeks on three separate occasions appeared lighter. Having achieved this degree of lightening, new areas of previously untreated skin with melasma were exposed to the same treatment protocol which also lightened the affected skin. After each laser treatment at 6.0 J/cm², 760 nm, 100 nsec pulse duration and a 3 mm diameter spot size, the treated skin area lightened substantially and the skin color more closely approximated that of normal skin coloration.

Case History No. 7

A 24 year old caucasian female presented herself for treatment of a grayish lesion which developed on her right shoulder following treatment using another pulsed dye laser. The clinical diagnosis of this lesion was post-inflammatory hyperpigmentation. The lesion was then exposed to the q-switched Alexandrite laser (760 nm), 100 nsec 3 mm diameter spotsize, on 2 occasions spaced 5–6 weeks apart, at fluences of 6.0 J/cm² at each visit. After the first visit, the gray hyperpigmentation lightened considerably. This gray discoloration completely cleared after a second laser treatment at 6.0 J/cm² using the Alexandrite laser at 760 nm, at a spotsize of 3 mm diameter, and a pulse duration of 50–100 nsec.

Summary of Alexandrite Laser Treatment of Benign Cutaneous Pigmented Lesions

The q-switched Alexandrite laser at 760 nm at pulse duration of between 50 and 100 nsec, fluences of between 2.5 and 7.0 J/cm² and a spotsize of 3 mm diameter will effectively and selectively remove some benign cutaneous pigmented lesions (cases 1–7). Not only is the abnormally pigmented cutaneous lesion selectively removed but the laser irradiated skin remains normal in color, texture, and mobility, with all the adnexae completely left intact.

The unique effect of the Alexandrite laser treatment method on skin with the benign cutaneous pigmented lesion is the fact that the laser irradiated skin turns white immediately following laser exposure. In addition to this, the epidermis remains intact. Then, a few minutes (2–10 minutes) after the laser exposure, the laser irradiated area becomes erythematous, elevated and edematous. By contrast, the surrounding normal skin exposed to the same laser parameters as those used to treat the benign cutaneous pigmented lesions does not become either discolored or edematous.

B. Treatment of Epidermal Nevus

Case History No. 8

A 25 year old caucasian female with linear bands of hyperpigmented papules on her right shoulder and chest, right upper arm and side of her trunk presented herself for treatment. The diagnosis was epidermal nevus. A test area was delineated on the anterior surface of her upper arm and tested using the Alexandrite laser (760 nm) at a pulse duration of 100 nsec. The initial test was performed at a fluence of 2.5 J/cm², and a spotsize of 3 mm diameter. The epidermal nevus appeared flatter when the patient returned at the 6 week follow-up period.

Three further areas of the lesion were then delineated. Two areas were exposed to the Alexandrite laser at an exposure over 100 nsec. One of these was exposed to 4.0 J/cm², and a 3 mm diameter spotsize; the second, to 20.0 J/cm² and a 1 mm diameter spotsize. There was some flattening of these two sites.

The third test area of epidermal nevus was exposed to a 50 nsec q-switched Alexandrite laser at 30.0 J/cm², and a 1 mm diameter spotsize; this produced significant flattening of the epidermal nevus at 6 weeks time following the laser exposure. Because this combination of laser parameters [a 1 mm diameter spot size, 30 J/cm², at 50 nsec] produced the best clinical result, larger areas of the epidermal nevus were treated using the Alexandrite laser at 50 nsec, 1 mm diameter spotsize at fluences of between 25 and 30 J/cm². Since that time, between 10 and 50 cm² areas of the epidermal nevus have been retreated a further 2–3 times, after which time the epidermal nevus has been completely removed and leaving adjacent normal skin unaltered. No recurrence of the tumor has been observed. These area were unlike those previously treated using the CO₂ laser where scar formation, loss of skin pigmentation and recurrence of the tumor were the clinical end result.

Summary of Alexandrite Laser Treatment of Epidermal Nevus

Epidermal nevus is a benign tumor of the epidermis. One problem inherent to the treatment of this tumor has been its recurrence several months following removal using a variety of treatments including surgery, dermabrasion, laser treatment in particular, the CO₂ laser.

The Alexandrite laser at 760 nm, 1 mm diameter spotsize, at a pulse duration of between 50 and 100 nsec and a fluence of between 20.00 and 30.00 J/cm² is able to effectively and permanently remove the epidermal nevus. There has been no evidence of recurrence of the tumor at the Alexandrite laser irradiated sites. Multiple retreatments to the same site are required to completely remove the epidermal tumor.

The clinical endpoint of significance is whitening of the laser irradiated skin. Unless the laser exposed skin turns white (matching the laser spotsize diameter) immediately after the laser exposure, the laser treatment will have minimal to no effect on the epidermal nevus. Following this whitening, the laser irradiated area will become erythematous and very edematous, a few minutes after laser exposure. Within a few days, the treated area will form very superficial "scabs" which will spontaneously "fall off" at around five to 14 days. No scarring or loss of pigment has resulted from the Alexandrite laser treatment of epidermal nevus (tumor) described in case history number 8.

C. Treatment of Tattoos

Case History No. 9

A 29 year old caucasian male with a professional tattoo on his chest which was tattooed with the words "ROCKY & ROCKY JR" using blue/black ink 9 years previously.

The Alexandrite laser was set at 760 nanometers with a pulse duration in the 50 to 100 nanosecond pulse duration range to cover a spot size of 3 millimeters diameters at fluences (energy densities) of 2–5 Joules per square centimeter. These operating parameters were used to treat different zones or parts of the tattoo as test sites. It was observed that the skin at the exposed test sites, including the hairs, turned grayish-white immediately after laser irradiation. This was accompanied by the apparent disappearance of the tattoo from the laser exposed site. The surface of the skin (i.e., the stratum corneum) remained intact and the skin surface did not perforate (burst open) immediately following laser exposure.

Within 5 minutes of laser exposure, the grayish/whitening which was present on the surface disappeared and the tattoo reappeared at the laser exposed site. Accompanying this reappearance, the laser irradiated site appeared "swollen" (edematous) and reddened.

At the four week follow-up visit, a thorough examination of the irradiated test skin area was made. No significant color change in the laser treated tattoo sites were observed. Another test site was delineated and exposed to 5 J/cm$^2$ using a 3 mm diameter spotsize. The exposed test skin site again turned grayish-white immediately after irradiation when then again disappeared from the treated skin surface about 5 minutes afterwards. The patient was then asked to return three weeks later for the next repeat visit.

At this subsequent three week visit, clearance of the tattoo treated previously at 5 J/cm$^2$ was noted. In addition, the laser treated exposed site appeared slightly lighter than normal skin. Because there were still remnants of tattoo at the treated site, the same skin area was again treated using a fluence of 4 J/cm$^2$. Section by section irradiations of the entire tattoo were then begun.

The tattoo sections responded with lightening to irradiations of 4 and 5 Joules per square centimeter on the initial occasion. Repeat irradiation treatments were then delivered to the same tattoo sections using these same fluences at time intervals ranging between two and six weeks.

The tattoo became lightened with each successive irradiation treatment in sequence, eventually clearing the entirety of the tattoo. The skin at the treated sites retained its normal skin color as well as its normal skin markings and elasticity throughout the irradiation treatment regimen.

Case History No. 10

A 34 year old caucasian male had multiple professional tattoos of several color (green, red, yellow, black, and orange) of 18 years' age on both his arms.

The patient stated that several colors had faded in the first two years after the tattoo was placed. The yellow color faded first followed by the fading of orange and red. At the time of initial treatment, the tattoo was blue-black in appearance.

The Alexandrite laser was used to test the effects of irradiating the green and black sections of the tattoo using fluences of 2, 4, and 5 J/cm$^2$ respectively. The initial response immediately following laser exposure was that the irradiated skin surface turned grayish-white. This was accompanied by swelling of each test site within 1-5 minutes of laser exposure. The grayish-white discoloration appeared over the next 5-10 minutes, after which time the tattoo reappeared and the laser exposed sites remained swollen. The time taken for the whitening/graying to disappear after which time the tattoo reappeared and the laser exposed sites remained swollen. The time taken for the whitening/graying to disappear after laser exposure was longer at the higher fluences, taking up to 20 minutes to disappear.

The best response with lightening was achieved using 4 and 5 Joules per square centimeter on the blue/black tattoo sections at an exposure time of 50-100 nsec. These skin areas have been repeatedly irradiated using the same energy densities and exposure time. Lightening of the tattoo continued with each irradiation treatment in series. In addition, some sections of the tattoo have already been cleaned of pigment leaving the skin at the irradiated site normal both in color and texture.

Treatment of the tattoo, section by section, is presently continuing. It is likely that it will be necessary periodically to increase the energy density (possibly up to 20 Joules per square centimeter) as the treatment program progresses, and as the tattoo pigment decreases in amount, and as the pigment aggregates fragment into smaller particles. It is expected that each skin section may require up to 15 or 20 repeat irradiation treatments to become completely cleared of the tattoo. A major benefit to the patient of this procedure is that the cleared skin in the treatment sections is indistinguishable from the normal adjacent, non-tattooed, skin in that person.

Case History No. 11

Amateur tattoos on both arms, on the back of the right hand, and on all four fingers and chest were created 37 and 40 years ago using Indian ink in a caucasian male now 53 years old. The index, middle, and fourth fingers were designated as the initial test sites. The treatment doses and lasers used as well as the follow-up treatments are outlined in Table 3 below.

TABLE 3

| FLUENCES USED TO TREAT INDIVIDUAL TATTOOS IN CASE HISTORY NO. 3* | | | | | |
| --- | --- | --- | --- | --- | --- |
| Date | Index | Middle | Ring | Fifth | Hand |
| 3/05 | 4 J/cm$^2$ | N/A | 5 J/cm$^2$ | N/A | N/A |
| 3/26 | 5 J/cm$^2$ | 5 J/cm$^2$ | 5 J/cm$^2$ | 5 J/cm$^2$ | 5 J/cm$^2$ |
| 4/14 | 4 J/cm$^2$ | 4 J/cm$^2$ | 4 J/cm$^2$ | 4 J/cm$^2$ | 4 J/cm$^2$ |
| 5/14 | 5 J/cm$^2$ | 5 J/cm$^2$ | 5 J/cm$^2$ | 5 J/cm$^2$ | 5 J/cm$^2$ |

*Other laser parameters remained constant.
Spot size = 3 mm diamters.
Pulse duration = 50-100 nsec.
Wavelength = 760 nm.
N/A = not attempted.

The tattoos at these individual sites lightened with each irradiation exposure except those skin areas irradiated on the initial visit of 3/05. The fluences employed on that occasion were varied to determine how differences in laser energy density would affect the degree of lightening achieved.

On the initial visit of 3/05, the treated skin turned grayish-white immediately after laser exposure at both 4 and 5 J/cm$^2$ respectively. Then, about 5-7 minutes after irradiation, the grayish-white coloration was replaced by the return of the pigmented tattoo at each of the treated test sites.

At the return visit of 3/26, very little change was seen in the previously irradiated skin sites and the laser fluence used on 3/05 was then increased by 1 J/cm$^2$, while keeping the other laser operating parameters constant. Again, the skin sites irradiated on this occasion turned grayish-white immediately after laser exposure. The patient was then asked to return in 20 days time for the next visit.

At the follow up visit of 4/14, a few areas of the previously irradiated skin appeared slightly lighter than the adjacent non-tattooed normal skin. Therefore, the laser fluence was decreased to 4 J/cm$^2$ using and exposure time of 50-100 nsec and a spot size of 3 mm in diameter. After treatment, the patient was to return in 30 days for his next visit.

On the visit of 5/14, however, very little change in color was observed at those skin sites irradiated on 4/14 using the 4 J/cm$^2$ energy density. Therefore, the fluence was again increased to 5 J/cm$^2$ while the other operating parameters of exposure time, spot size, and light wavelength remained the same. Treatment of the tattoo, section by section, was then begun.

It is expected that increases in laser fluence up to 20 J/cm$^2$ will be required to clear the tattoo entirely as it lightens in color. Also, it is likely that multiple treatments involving up to 20 return visits will be needed at intervals of 2-10 weeks between each irradiation treatment in order to complete this regime.

Case History No. 12

An amateur tattoo with the words "JOHN" on the left outer thigh of a of a 33 year old caucasian female was created 13 to 14 years ago using blue Indian ink. The whole lesion, which was approximately 1.5×3.0 cm, was exposed to light from the Alexandrite laser at 760 nm, 50-100 nsec exposure time, 3 mm diameter spotsize, and a fluence of 5 J/cm$^2$. The skin immediately following laser exposure turned grayish-white, this coloration gradually disappearing after 5-10 minutes and after which the treated sites appeared swollen, raised, and pink. When the tattoo was examined at the second visit sex weeks following the initial treatment, the whole tattoo had lightened and thus was retreated using the same laser operating parameters. Laser exposures of the tattoo now continue with return visits for treatment scheduled between to and eight week intervals and with increasing irradiation fluence until the whole tattoo clears completely. It is expected that between 8 and 12 treatments will be required to completely clear the tattoo.

Case History No. 13

A professional tattoo formed as two hands clasped together was placed 30 years ago on the right forearm of a caucasian male now 47 years old. The right side of the tattoo was purposely exposed to laser light from the conventional ruby laser while the left side of the tattoo was exposed to laser light from the Alexandrite laser. The operating parameters of both laser irradiations were similar; each irradiation used a fluence of 4 J/cm$^2$ and an exposure time of 50-100 nsec.

At the first return visit 4 weeks later, the patient reported that the right side of the tattoos exposed to the ruby laser oozed shortly after initial irradiation; and that the oozing was replaced by crusts on the skin surface within 1-2 days of treatment. The skin crusts persisted for nearly two weeks and then gradually fell off leaving the skin area "whiter" than the normal adjacent skin. By the time of this first return visit (4 weeks after initial irradiation), a lightening of both the right and left sides of the tattoo was observed.

The treatment procedure was then purposely repeated on this first return visit; the right and left sides of the tattoo were again irradiated individually using the ruby laser and Alexandrite laser and the same operating parameter as on the initial treatment occasion. The patient was then asked to return after four additional weeks for his next visit.

On the third visit (8 weeks after the initial treatment), the right side of the tattoo exposed to the ruby laser appeared more hypopigmented—that is, whiter in color and more shiny in appearance—than the left side of the tattoo irradiated previously using Alexandrite laser light. In addition, the skin on the Alexandrite laser treated left side was not only completely cleared of the tattoo but also appeared normal both in skin color and skin texture with respect to the untreated skin areas immediately adjacent. However, the Alexandrite laser treated skin was substantially different and in marked contrast to the ruby laser exposed skin which demonstrated a potentially permanent loss of normal skin pigmentation as a consequence of irradiation.

It is of major significance that the left side of the tattoo irradiated with the Alexandrite laser light has apparently cleared completely after only two irradiation treatment occasions; and has left the treated skin area of the patient in a normal condition as to both coloration and texture. It is also noteworthy that the Alexandrite laser treated skin did not cause any oozing of the skin tissue; did not become crusty or hard as a consequence of the irradiation; and did not become either hypopigmented or scarred.

The remainder of the tattoo of the patient will now be treated section by section using only Alexandrite laser light under the earlier described operating parameters. Treatment visits will be scheduled repeatedly at 2-8 week time intervals with increasing irradiation fluence if necessary until the entirety of the tattoo is completely cleared. It is expected that approximately 10-15 treatment occasions will be required to achieve complete clearance of the entire tattoo.

Case History No. 14

A 42 year old caucasian male had a panther professionally tattooed on his upper arm 25 years earlier. Most of the tattoo was outlined and filled in with blue/black in. The tip of the panther was irradiated using a fluence of 2.5 Joules per square centimeter for 50-100 nsec using the Q-switched Alexandrite laser while another part of the tail was irradiated using the ruby laser with light at 694 nanometers using fluences of 2.0 and 3.5 Joules per square centimeter for the same time exposure. On the return visit, approximately six weeks later, very little change was observed on the skin at the Alexandrite laser irradiated area but some lightening of the skin was observed at the ruby laser irradiated site. At this return visit also, the right leg and lower half of the body of the panther tattoo was exposed to light from the Alexandrite tattoo was exposed to light from the Alexandrite laser at a fluence of 4 Joules per square centimeter while the left leg of the panther tattoo was exposed to the ruby laser at a fluence of 4 Joules per square centimeter, both irradiations being of 50-100 nsec exposure time. The patient was then scheduled to return in 4 weeks.

On the occasion of his third visit, a direct comparison of the ruby laser treated skin and the Alexandrite laser irradiated skin was made in detail. Significant lightening was observed at all the treated skin sites. However, areas treated using the ruby laser had punctuate openings at the surface of each site through which oozed blood and serum. These areas subsequently crusted over; some of this crusting was still evident after ten weeks. By contrast, the skin remained intact at every site exposed to the Alexandrite laser in spite of the fact that the skin turned a grayish white immediately after laser irradiation on each occasion.

Another difference noted at the third visit was the fact that the ruby laser irradiated site appeared hypopigmented compared to the Alexandrite irradiated sites. These findings suggest that the Alexandrite laser beam penetrated deeper into the skin than the ruby laser beam. Therefore, because the tattoo pigment most often "aggregates" around dermal vessels in the papillary dermis, the Alexandrite is a more efficient laser for destroying pigment than the ruby laser. This is because some of the ruby laser's energy will be lost through absorption by more superficial cutaneous structures such as stratum corneum and epidermis. When this happens, very little energy will be left for absorption by structures in the dermis. Moreover, it is evident that short pulses at high powers are needed to fragment dermal tattoo pigment. Because the ruby laser will have lost some of its energy at the surface, it will be less efficient at breaking up the tattoo fragment in the dermis. In order to be able to break up the tattoo pigment, higher doses will be required; and when high doses are used, then more damage will be induced at the skin surface. This damage consequently will heal by scar formation.

This tattoo will now be treated using increasing doses of Alexandrite laser light alone at two to eight weekly intervals for an expected 15-20 treatment visits at which time the tattoo will be completely cleared.

The present invention is not to be restricted in form nor limited in scope except by the claims appended hereto.

What I claim is:

1. A laser treatment method for removing pigment containing lesions from the skin of a living human, said method comprising the steps of:

irradiating on a first occasion a chosen treatment site on the skin of a living subject of about 1-100 millimeters in diameter with a beam of pulsed light from a laser delivery system, said pulsed light having a wavelength from about 700-1,100 nanometers, fluences of about 1-50 Joules per square centimeter, and a pulse duration of about 1-300 nanoseconds;

maintaining said irradiation to disrupt at least one pigment containing lesion on the chosen treatment site on the skin of the living human until a color change endpoint on the skin surface is achieved by said laser light treatment while largely avoiding the destruction of normal skin structures and cells;

allowing the skin at said irradiated treatment site to heal for a time period not less than about 7 days and not more than about 70 days; and then irradiating on at least one subsequent occasion the chosen treatment site on the skin of the living human with another pulsed beam of laser light having a wavelength from about 700-1,100 nanometers, fluences of about 1-50 Joules per square centimeter, and a pulse duration of about 1-300 nanoseconds, said subsequent irradiation occasion being repeated as necessary to achieve substantial clearance of the chosen treatment site on the skin.

2. A laser treatment method for removing pigment containing lesions from the skin of a living human, said method comprising the steps of:

irradiating on a first occasion a chosen treatment site on the skin of a living subject of about 1-100 millimeters in diameter with a beam of pulsed light from a laser delivery system, said pulsed light having a wavelength from about 700-1,100 nanometers, fluences of about 1-50 Joules per square centimeter, and a pulse duration of about 1-300 nanoseconds;

maintaining said irradiation to disrupt at least one pigment containing lesion on the chosen treatment site on the skin of the living human until a color change endpoint on the skin surface is achieved by said laser light treatment while largely avoiding the destruction of normal skin structures and cells;

allowing the skin at said irradiated treatment site to heal for a time period not less than about 7 days and not more than about 70 days; and then irradiating on multiple subsequent occasions the chosen treatment site on the skin of the living human with another pulsed beam on laser light having a wavelength from about 700-1,100 nanometers, fluences of about 1-50 Joules per square centimeter, and a pulse duration of about 1-300 nanoseconds, said subsequent irradiation occasion being repeated as necessary to achieve substantial clearance of the chosen treatment site on the skin.

3. The laser treatment method as recited in claim 1 or 2 wherein said irradiation of the chosen treatment site on the skin is controlled to avoid causing whiteness and pitting of the skin.

4. The laser treatment method as recited in claim 1 or 2 wherein said irradiation on the first occasion employs a lesser fluence value than said irradiation on said second occasion.

5. The laser treatment method as recited in claim 1 or 2 wherein said irradiation on said first occasion employs a greater fluence value than said irradiation on the second occasion.

6. The laser treatment method as recited in claim 1 or 2 wherein said irradiation employs laser light having a wavelength of from 750-800 nanometers.

7. The laser treatment method as recited in claim 1 or 2 further comprising applying a topical antibiotic preparation to the chosen treatment site on the skin after each irradiation occasion.

* * * * *